United States Patent [19]

Sibrava

[11] 4,055,259

[45] Oct. 25, 1977

[54] SAMPLE TRANSPORT WITH ROTARY AIR INTERLOCK CHARGING AND DISCHARGING MEANS

[75] Inventor: Joseph Sibrava, Fairfield, Conn.

[73] Assignee: The Perkin-Elmer Corporation, Norwalk, Conn.

[21] Appl. No.: 663,537

[22] Filed: Mar. 3, 1976

[51] Int. Cl.² .................... G01N 1/02; G01N 31/12
[52] U.S. Cl. ........................ 214/17 A; 23/253 PC; 73/422 GC; 214/17 B; 214/29
[58] Field of Search .............. 214/17 R, 17 A, 17 B, 214/17 C, 17 CB, 17 CC, 29; 23/253 PC, 259, 288 E; 221/76, 82, 83, 225; 222/194, 370, 564; 141/67; 73/422, 15 R, 15.4, 422 CC, 190 R; 250/288

[56] References Cited

U.S. PATENT DOCUMENTS

| 2,258,866 | 10/1941 | Sanford | 221/82 |
| 2,258,866 | 10/1941 | Sanford | 221/8.2 |
| 2,706,148 | 4/1955 | Knapp | 214/17 B X |
| 3,102,665 | 9/1963 | Zeiss | 222/239 |
| 3,401,552 | 9/1968 | Ruchelman | 73/422 GC X |
| 3,498,107 | 3/1970 | Kim et al. | 73/422 GC X |

FOREIGN PATENT DOCUMENTS

| 463,142 | 11/1968 | Switzerland | 73/19 |
| 1,170,535 | 11/1969 | United Kingdom | 73/422 GC |

Primary Examiner—Robert J. Spar
Assistant Examiner—Carl Rowold
Attorney, Agent, or Firm—S. A. Giarratana; F. L. Masselle; J. D. Crane

[57] ABSTRACT

A compact, sealable sample transport apparatus for conveying material from a supply to a combustion chamber, includes an elongated ladle member longitudinally moved in a conduit to the combustion chamber and coacting rotary magazine and transfer plate members, sealed with respect to one another so as to enable discrete analytical specimens to be loaded into and, after analysis, discharged from the ladle member without substantial exposure of the interior of the apparatus to the ambient atmosphere.

7 Claims, 1 Drawing Figure

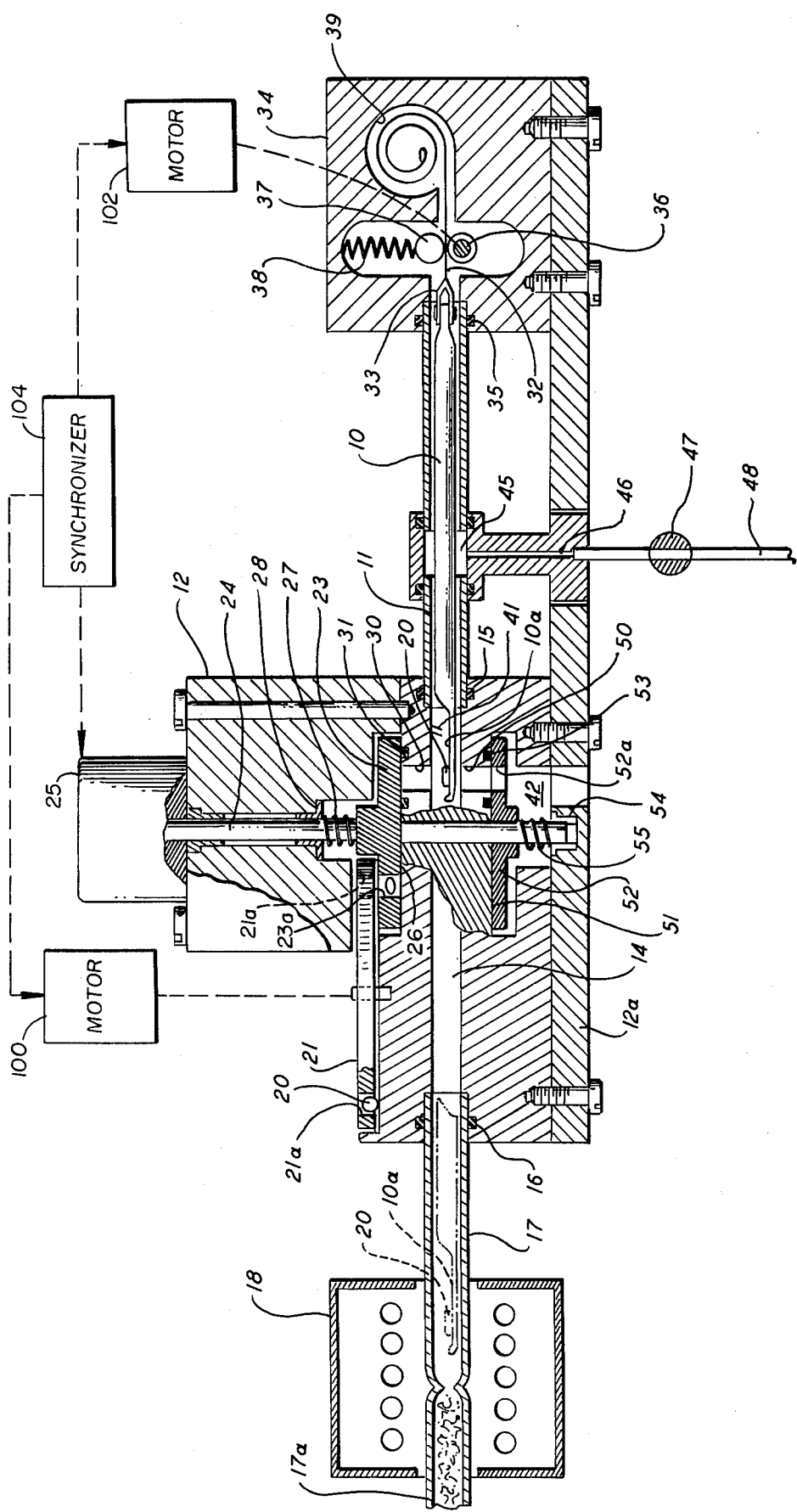

SAMPLE TRANSPORT WITH ROTARY AIR INTERLOCK CHARGING AND DISCHARGING MEANS

BACKGROUND OF THE INVENTION

In a co-pending application for U.S. Letters Patent, Ser. No. 654,426 filed Feb. 2, 1976 by I. E. Dolgen and assigned to the same assignee as the present invention there is described and claimed an apparatus for transporting small amounts of material from a supply to another location a short distance away. In that apparatus a ladle type sample transport conveys small discrete analytical specimens, contained in pellets or capsules, from a supply magazine to the combustion chamber of a combustion elemental analysis instrument in which the sample material is burned and the combustion products analyzed to determine quantitatively the presence of a particular element, e.g., carbon, hydrogen, nitrogen.

The present invention relates to sample transport apparatus of the type described in the aforementioned copending application and, in particular, to a subsystem thereof for transferring the sample pellets to the ladle and discharging combustion residue from the ladle while maintaining the interior of the total transport apparatus sealed against entry of the ambient atmosphere. For convenience and clarity of understanding, the transport system of this invention is hereinafter described with particular reference to its adaptation for use with such a combustion elemental analytical instrument but it will be understood that it would also be useful in other applications.

In order to provide accurate analysis with the aforesaid types of analytical instruments discrete samples are customarily burned in a controlled atmosphere, e.g., in pure oxygen, at a particular pressure; accordingly, it is necessary to provide for purging the combustion volume between successive burnings and to seal this volume against entry of the ambient atmosphere. Obviously, it is necessary to provide access to the chamber in order to introduce samples and remove the ash residue after combustion and analysis has been accomplished. It is also highly desirable that the introduction of samples and removal of combustion residue be effected in an automatic sequence.

At present, in one known type of combustion analysis instrument, material to be analyzed is loaded into a platinum capsule which is then placed in a ladle-type boat. The end of a transfer tube is opened and the loaded boat is inserted. The tube is closed and a purge gas is circulated through the system to eliminate contaminants entering when the tube is opened; then the loaded boat is advanced through the transfer tube to the combustion chamber by means of a magnet moved manually along the outside of the tube. After combustion, the boat with the capsule containing ash is magnetically withdrawn from the combustion chamber and back to the loading end of the tube which is opened for removal of combustion residue and introduction of a new sample capsule. Due to the foregoing manual loading and feeding and the need to purge the system for each load, the procedure is cumbersome, tedious and very time-consuming when a series of analyses is to be performed.

Automatic loading systems have been proposed in which some sort of mechanical transport mechanism, adapted for automated sequential operation, is employed but in previously known mechanical systems the mechanisms for carrying capsules from a magazine to the combustion chamber and then to a residue receiving and holding tube or cavity are rather complex and take up a disproportionate amount of space. Moreover, the automation of sample loading represents only a partial solution to the problem of expediting analysis where extensive purging is required between each sample.

It is, therefore, a general object of the present invention to provide an automatic sample transport apparatus which overcomes or mitigates the shortcomings of comparable prior art devices as discussed above. A more specific object is the provision of automatic sampling apparatus for analytical instruments that is compact, mechanically simple, and reduces or eliminates the need for purging to maintain a controlled atmosphere.

SUMMARY OF THE INVENTION

To the accomplishment of the foregoing and other objects and advantages which will become apparent as this description proceeds, the present invention contemplates an automatic sample apparatus for conveying a series of discrete sample quantities to and from an analysis chamber. The apparatus comprises a conduit having one end adapted to be sealingly coupled in flow communication with the analysis chamber, the conduit having a sample inlet passage extending transversely thereinto at a point remote from the chamber coupling end of the conduit. A sample discharge passage is provided on the opposite side of the conduit and aligned with the sample inlet aperture.

A first transfer plate disposed in normally occluding relationship to the sample inlet passage contains a sample receiving aperture and is mounted for displacement to a loading position in which the aperture registers with the sample inlet passage. A second transfer plate is disposed in normally occluding relation to the sample discharge passage and contains an aperture adapted to receive the residue of a sample subsequent to analysis in the analysis chamber. The second transfer plate is mounted for displacement to a sample discharge position in which the aperture in the plate registers with the sample discharge passage and means are provided for sealing the first and second transfer plates around and with respect to the inlet and outlet sample passages, respectively. Means are also provided for displacing the transfer plates in timed relation to one another to bring the aperture of the first place into registration with the sample inlet passage while the sample discharge passage is occluded by the second transfer plate and the aperture of the second transfer plate into registration with the sample discharge passage when the sample inlet passage is occluded by the first transfer plate.

BRIEF DESCRIPTION OF THE DRAWINGS

The single FIGURE of drawing is a partially schematic longitudinal section of a sample transport apparatus in accordance with a preferred embodiment of the present invention with certain portions broken away to illustrate underlying structure.

DETAILED DESCRIPTION OF THE INVENTION

Referring to the drawing, a sample transport in accordance with this invention includes an elongate sample transport member or ladle 10 slideable in a main conduit made up of aligned segments 11 and 14. Specifically, the left-hand end (as viewed in the drawing and sometimes referred herein as the "forward" end) of a tubular member defining segment 11 is connected into a sample-transfer housing 12, being coupled in coaxial relation with the right-hand end of a passage 14 through the housing 12 by a connection sealed with an O-ring 15. The forward end of the housing passage 14 is coupled through a sealed connection provided by an O-ring 16 to an analysis chamber, which, in the embodiment illustrated, is the combustion tube 17 of a combustion elemental analyzer instrument (of which are shown only the combustion tube 17 and a furnace portion 18 into which the tube extends.)

In such a combustion analysis instrument, an analytical sample is inserted into combustion tube 17 to a point therein that is within furnace portion 18. In normal operation, tube 17 is then purged, if necessary, to eliminate contaminants by flowing a purge gas through it (suitable ports and valves being provided for this purpose) and the tube is filld with a gas that provides the controlled atmosphere in which the sample is to be burned for the analysis. For example, in testing for carbon, hydrogen, or nitrogen, the sample is burned in an oxygen atmosphere.

As the sample burns, the gaseous combustion products are drawn into the analysis portion (not shown) of the instrument through a combustion tube extension 17a which extends from the tube 17. Thereafter, the solid combustion residue of the sample are withdrawn from the furnace portion 18, back through the combustion tube 17.

As previously mentioned, the sample transport mechanism of this invention is particularly adapted to provide a compact, mechanically simple system for inserting discrete sample quantities into the combustion tube or chamber of the foregoing type, and for removing solid combustion residue therefrom. For this purpose, the forward end of transport member 10 has a spoon-like sample holding cavity or depression 10a into which a sample 20 of material to be tested is deposited. The sample material normally is provided in the form of pellets, in order to have successive samples of all the same weight or volume. In one usual form, the material to be analyzed is loaded into platinum capsules which among other things are not reactive nor consumed by the burning and contain the solid combustion residue for convenient withdrawal from the furnace. A supply of sample pellets is contained in a magazine which, in the embodiment illustrated, takes the form of a discoid turntable member 21 having a concentric ring of sample-receiving apertures 21a adjacent its periphery into which pellets 20 are loaded. Motor means 100 are provided for rotating the turntable 21.

Magazine turntable 21 is mounted on a surface of housing 12 in a position for one edge portion to overlap an edge portion of a circular transfer plate 23 which is also rotatably supported in housing 12 and which has at least one pellet-receiving aperture 23a therethrough. Transfer plate 23 is rotatively mounted in housing 12 by means of a shaft 24 to which it is fixed and which is driven by a motor 25. Transfer plate motor 25 may be connected (by means not shown) to rotate the magazine turntable 21 also instead of utilizing a separate motor for the turntable.

The bottom surface of plate 23 is urged against a surface 26 of housing 12 by means of coil spring 27 disposed around shaft 24 and compressed between the top of the plate and a shoulder 28 in the housing. It will be noted from the drawing that turntable 21 is disposed in a plane parallel to and slightly above transfer 23 with its axis of rotation parallel to the axis of shaft 24; moreover, the spacing of these axes and the respective radial distances of apertures 21a and 23a therefrom are such that, at one point of rotation of the magazine turntable and transfer plate, one of the apertures 12a of the former registers with the aperture 23a of the latter. At this point, a sample pellet is transferred from the turntable to transfer plate aperture 23a.

A sample inlet passage 30 in housing 12 extends transversely of and opens into conduit segment 14; the passage underlies and is normally occluded by transfer plate 23. Passage 30 is sealed with respect to the underside of plate 23 with an O-ring 31 or other suitable sealing means. The axis of passage 30 is parallel to and spaced from the axis of shaft 24 by the same radial distance as aperture 23a; consequently, at one point of the rotation of plate 23, aperture 23a registers with passage 30 permitting a sample pellet 20 to fall through the passage to be received in ladle cavity 10a, when the latter is positioned below the passage as shown in the drawing.

From the structure thus far described, it will be seen that motor 25 and, if separate, the motor (not shown) employed to drive turntable 21, can be controlled as part of a sequence of programmed steps in the automated operation of the analytical instrument with which the sample transport apparatus of this invention is utilized in order to transfer successive pellets from apertures 21a of the turntable to ladle cavity portion 10a for the start of an operative cycle of the instrument.

Sample transport member 10 is displaceable in conduit 11, 14 and combustion tube 17, between a retracted position (shown in full lines) in which the sample cavity 10a receives pellet 20 from the magazine turntable 21 in the manner just described and an advanced position (indicated in broken line) in which cavity 10a, with a pellet 20 therein, is within furnace 18, by means of a flexible tape 32 attached to the rearward end of the transport member, as by means of a clevis and pin connection 33.

To this end, tape 32 is moved out of and back into a storage housing 34, which is sealed to the rear end of conduit segment 11 by an O-ring 35, by drive means within the housing consisting of a drive roller 36 and a cooperating idler roller 37 between which the tape passes. Idler 37 is urged toward drive roller 36 by a spring 38 to provide the requisite frictional engagement with the tape 32. As the rearwardmost end of the tape 32 is retracted into the housing 34, it is caused to coil on itself by the cylindrical configuration of a storage chamber 30 in which the tape is received. Thus, thus storage space required for a tape 32 of sufficient length to move transport member 10 the requisite distance is minimized.

Drive roller 36 may be powered by an electric motor 102 which, like transfer plate drive motor 25, may be actuated in an automated sequence by a synchronizer 104 for moving the ladle member 10 to its different positions as required for a cycle of operation of the instrument.

Below conduit segment 14, housing 12 contains a sample discharge passage 50 extending transversely of the conduit and in coaxial alignment with passage 30. The upper end of passage 50 opens into conduit segment 14; the lower end opens in a plane surface 51 of housing 12 and is normally occluded by a second transfer plate 52 which is axially slidable along the lower end of shaft 24 but is restrained from turning thereon, as by a spline or key and slot interface, not shown. Transfer plate 52 contains at least one aperture 52a so located with respect to the axis of shaft 24 as to register with passage 50 at one point of its rotation, as shown in the drawing, from which it will be seen that aperture 52a is angularly displaced relative to aperture 23a in upper transfer plate 23 so that registration of the apertures with their respective passages 30 and 50 never occurs simultaneously. Passage 50 is sealed with respect to the upper surface of lower transfer plate 52 with an O-ring 53 or other suitable sealing means.

The lower end of shaft 24 is journaled in a closure plate 12a forming the bottom of housing 12 by means of a suitable bearing 54. A coil spring 55, compressed between closure plate 12a and the underside of transfer plate 52, urges the transfer plate upwardly against a surface 51.

An open volume or chamber 42 is formed in housing 12 below passage 50 to receive sample residue in a manner which will become apparent as this description proceeds.

A wiper blade 41 is pivotally mounted in conduit segment 14 to pivot down into the sample holding cavity 10a. Wiper blade 41 is provided with sufficient clearance to ride over the top of the transport member 10 during its advance stroke; when the transport member retracts, wiper blade 41 rides down into cavity 10a sweeping residue out of the cavity and down into passage 50.

In flow communication with conduit segment 11 via an annular space 45 is duct 46; a tubular conduit 48 containing a valve 47 connects duct 46 to a source of gas, (not shown) e.g., oxygen, under pressure.

In operation, the instrument to which the sampling apparatus of this invention is operatively connected and the interior of the transport mechanism are first purged or flushed by forcing air or gas under pressure through it. Gas applied through conduit 46 and valve 47 may be used for this purpose. When the purging is completed, valve 47 is opened sufficiently to supply gas, such as oxygen, to conduit 11, 14 under pressure that is adequate at least to create a positive pressure relative to ambient, so as to prevent air or contaminants from entering the system.

Next, sample transport member 10 is positioned with its cavity 10a in line with the passage 30 and shaft 24 rotated to bring aperture 23a containing a pellet 20 into registration with this passage so that the pellet drops down through and into cavity 10a.

At this time, passage 50 is covered by lower transfer plate 52; shaft 24 continues to rotate so that passage 30 is also occluded, by upper transfer plate 23, as soon as the pellet 20 has dropped from aperture 23a. Transport member 10 is then advanced by drive tape 32 to move cavity 10a and the pellet 20 contained therein into furnace 18 for the combustion. After combustion and after the gaseous combustion products have been withdrawn into the analytical portion of the instrument, through combustion tube extension 17a, the analytical portion of the instrument is shut off from the furnace portion by suitable valve means (not shown). Then transport member 10 is retracted at least to the point at which wiper blade 41 operates to sweep residue out of the cavity 10a into passage 50 which, at this time, is still occluded by lower plate 52; rotation of shaft 24 then brings aperture 52a into registration with passage 50 permitting the residue to fall into chamber 42. Continued rotation of shaft 24 causes plate 52 to close off passage 50 before sample inlet passage 30 is opened to repeat the cycle.

The synchronizer 104 is coupled to the motors 25, 100 and 102 to synchronize their operation so as to move the turntable member 21, the transfer plates 23 and 52 and the sample transfer member 10 in timed relation to cause the apparatus to operate as described. The synchronizer 104 takes any suitable form wellknown in the art for synchronizing the operation of three motors and may include electromechanical, electronic or other suitable means for synchronizing the motor operation to perform the following operations. In particular, the motors 100 and 25 are controlled so the sample receiving aperture 21a registers with the sample receiving aperture 23a enabling a sample to be transferred from the turntable 21 to the transfer plate 23. The shaft 24 is thereafter rotated by the motor 25 so the sample receiving aperture 23a registers with the sample inlet passage 30 while the transport member 10 underlies the passage 30. At the same time, the sample discharge passage 52a is occluded. Once the sample is transferred to the transport member 10, the motor 102 drives the sample to the analysis chamber. After testing is complete, the motor 102 is again actuated to move the transport member 10 away from the analysis chamber to a point where the sample cavity on the transport member passes the passage 50. Thereafter, the motor 25 is again actuated to align the passage 52a with the passage 50 thereby allowing any sample residue to be discharged.

It will be seen that the tape driven sample transport of this invention is sealed from outside atmosphere, is adapted to feed a succession of pellets to the desired location from a magazine by mechanical means which may be operated automatically, and contains mechanism for such operation in a minimum of space.

What we claim is:

1. An automatic sampling apparatus for conveying a series of discrete sample quantities to and from an analysis chamber comprising:

means defining a conduit having one end adapted to be sealingly coupled in flow communication with said chamber;

a sample inlet passage extending transversely into said conduit at a point remote from said one end and a sample discharge passage on the opposite side of said conduit, aligned with the sample inlet passage;

a first transfer plate disposed in normally-occluding relationship to said sample inlet passage, said transfer plate containing a sample-receiving aperture;

means mounting said first transfer plate for displacement to a loading position in which said aperture registers with said sample inlet passage;

a second transfer plate disposed in normally-occluding relationship to said sample discharge passage, said second transfer plate containing an aperture adapted to receive the residue of a sample quantity subsequent to analysis in said chamber;

means mounting said second transfer plate for displacement to a sample discharge position in which the aperture in the second transfer plate registers with the sample discharge passage;

means for sealing said first and second transfer plates around and with respect to the inlet and outlet sample passages respectively, said sealing means including a spring for each said transfer plate and said springs being compressed against said transfer plates respectively to exert the sealing forces in converging directions along the alignment axis of said sample passages; and means for displacing said transfer plates in timed relation to one another to bring the aperture of the first plate into registration with the sample inlet passage while the sample discharge passage is occluded by the second transfer plate and the aperture of the second transfer plate into registration with the sample discharge passage when the sample inlet passage is occluded by the first transfer plate.

2. Apparatus according to claim 1 further including a sample transport member having a sample holding cavity and being slideable in said conduit between a position in which said cavity is disposed between said sample inlet and sample discharge passages and a second position in which the cavity is introduced into said chamber.

3. Apparatus according to claim 2 further including a magazine for holding a plurality of discrete sample quantities and operable to introduce such sample quantities individually in sequence into the aperture in said first transfer plate while said aperture is out of registration with said sample inlet passage.

4. Apparatus in accordance with claim 3 wherein said transfer plates are of generally circular configuration and said first and second transfer plate mounting means includes a single shaft on which said plates are nonrotatably mounted in coaxially spaced relationship and with the respective apertures in said plates angularly displaced from one another.

5. Apparatus according to claim 4 wherein said magazine comprises a discoid turntable member having a concentric ring of sample receiving apertures therein, said member mounted for rotation in a plane parallel to the plane of said first transfer plate with its axis of rotation so disposed with respect to the axis of said shaft that peripheral portions of said turntable member and transfer plate overlap and the sample receiving apertures of the magazine member register sequentially with the aperture of the first transfer plate when said first transfer plate aperture is out of registration with said sample inlet passage.

6. Apparatus according to claim 5 further comprising means for moving said turntable member, first and second transfer plates, and sample transport member in timed relation whereby the sample receiving aperture in the turntable member registers with the aperture in the first transfer plate enabling a sample quantity to enter the first transfer plate aperture from the turntable member; said shaft is rotated to bring the aperture of the first transfer plate into registration with the sample inlet passage while the transport member cavity underlies said passage and the sample discharge passage is occluded by the second transfer plate; rotating said shaft to effect occlusion of both said sample inlet and sample discharge passages by said first and second transfer plates, respectively, and concomitantly sliding the sample transport member to bring the cavity therein to the analysis chamber; sliding said sample transport member away from the analysis chamber to a point where the sample cavity thereof is moved beyond said passages in the direction away from said chamber while the sample discharge passage is occluded by the second transfer plate; and rotating said shaft to bring the aperture in the second transfer plate into registration with the sample discharge passage to enable discharge of sample residue therefrom.

7. Apparatus according to claim 6 further including a means to dislodge the residue of a sample quantity from said cavity as said cavity is moved beyond said sample inlet and discharges to cause such residue to enter the sample discharge passage.

* * * * *

UNITED STATES PATENT AND TRADEMARK OFFICE
CERTIFICATE OF CORRECTION

PATENT NO. : 4,055,259
DATED : October 25, 1977
INVENTOR(S) : Joseph Sibrava

It is certified that error appears in the above-identified patent and that said Letters Patent are hereby corrected as shown below:

Column 3, line 19, delete "filld" and insert in place thereof --filled--.

Column 4, line 1, after "transfer" and before "23" insert --plate--.

Column 4, line 35, delete "pellet" and insert in place thereof --pellets--.

Column 4, line 52, before "in" delete "30" and insert in place thereof --39--.

Column 4, line 52, after "Thus" and before "storage" delete "thus" and insert in place thereof --the--.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks